United States Patent
Lehmann et al.

(10) Patent No.: US 6,324,259 B1
(45) Date of Patent: Nov. 27, 2001

(54) SCATTERED-RAY GRID, PARTICULARLY FOR A MEDICAL X-RAY DEVICE, AND A METHOD OF DETERMINING THE POSITION OF THE ABSORPTION ELEMENTS OF A SCATTERED-RAY GRID

(75) Inventors: Volker Lehmann; Wolfgang Keller, both of München (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/564,463

(22) Filed: May 3, 2000

(30) Foreign Application Priority Data

May 3, 2000 (DE) .............................................. 199 20 301

(51) Int. Cl.$^7$ ...................................................... G21K 1/10
(52) U.S. Cl. ................................................................ 378/154
(58) Field of Search ..................................... 378/154, 155

(56) References Cited

U.S. PATENT DOCUMENTS

| | | | |
|---|---|---|---|
| 1,381,521 | * 6/1921 | Tousey | 378/154 |
| 1,891,332 | * 12/1932 | Mannl | 378/154 |
| 4,969,176 | * 11/1990 | Marinus | 378/149 |
| 6,018,566 | * 1/2000 | Eberhard et al. | 378/154 |
| 6,031,893 | 2/2000 | Schmetow | 378/154 |
| 6,047,044 | 4/2000 | Lehmann et al. | 378/154 |

FOREIGN PATENT DOCUMENTS

WO 99/31674 * 6/1999 (DE) ............................... G21K/1/02

* cited by examiner

Primary Examiner—Robert H. Kim
Assistant Examiner—Allen C. Ho
(74) Attorney, Agent, or Firm—Schiff Hardin & Waite

(57) ABSTRACT

A scattered-ray grid has a carrier with absorption elements arranged thereon in spaced rows which proceed essentially spoke-like relative to a grid center. Except for one or more rows which originate at the grid center, the individual rows of the scattered-ray grid, or of substantially identical grid sectors of the scattered-ray grid each originate from respectively different radii. The origin of each row is situated in an angle section, which is determined on the basis of at least two points lying on a circle, or an arc of circle, with a predetermined radius and which is divided in a predefined ratio for determining the position of the origin. The predetermined radius is incremented in a stepwise manner to define respective origins for all of the rows.

22 Claims, 3 Drawing Sheets

SCATTERED-RAY GRID, PARTICULARLY FOR A MEDICAL X-RAY DEVICE, AND A METHOD OF DETERMINING THE POSITION OF THE ABSORPTION ELEMENTS OF A SCATTERED-RAY GRID

BACKGROUND OF THE INVENTION

1. Field of the Invention

The present invention relates to a scattered-ray grid, particularly for a medical X-ray device, of the type having a carrier with absorption elements, particularly in the form of lead elements, which are arranged in spaced rows, as well as to a method for determining the position of the absorption elements in a scattered-ray grid.

2. Description of the Prior Art

In radiographic technology, particularly medical diagnostics, scattered-ray grids are frequently utilized to attenuate the scattered radiation which is always present with the primary radiation. The grids that are currently used most are composed of a sequence of line-like radiation absorption elements in the form of lead lamellae, which, alternately, are coated with lamellae made of a base material. X-rays that are incident in the plane of the lamellae are only insignificantly attenuated by the base material. By contrast, the lead lamellae highly absorb radiation that is obliquely incident. Since such lead lamellae generate unavoidable lines on the radiograph and since the number of lines per centimeter is limited due to manufacturing reasons, it has been suggested to use pins made of lead or another absorption material arranged in rows, the pins being spaced apart, instead of using lead lamellae in a silicon base material. Such scattered-ray grids are known from the German OS 197 26 846 and OS 197 29 596, for example.

German OS 197 26 846 describes a configuration concerning the arrangement of the pins (and thus of the rows), wherein the rows extend to the center of the grid in a spoke-like manner. In this arrangement, many rows start at the same radius. The density of the absorption elements (seen in the radial direction) considerably varies as a result and grey tone discontinuities also occur, and the row spaces (seen in the tangential direction) significantly vary as well. This has a disadvantageous effect on the entire absorption behavior of the grid and therefore on the image quality.

SUMMARY OF THE INVENTION

An object of the present invention is to provide a scattered-ray grid, which is improved compared to known scattered-ray grids with respect to the arrangement of the absorption element rows.

This object is achieved in accordance with the invention in a scattered-ray grid of the type described above wherein, inventively, the rows extend essentially radially from a center region and wherein, apart from one or more rows starting in the center point, the individual, identically structured rows of the scattered-ray grid or of the grid sectors of the scattered-ray grid proceed from starting points at respectively different radii, and wherein the origin (starting point) of each row is situated in an angle section, the angle section being determined by two points lying on a circle (or arc thereof) with a predetermined radius and which is divided in a predefined ratio for determining the position of the origin. The predetermined radius is incremented in a stepped manner to define the respective origins for all of the rows.

In the inventive scattered-ray grid, the origins of the lines, which all extend in the direction of the grid center, therefore produce an asterisk-shaped configuration, the lines respectively starting at different radii with respect to the grid center, so that a scattered-ray grid results which is significantly more homogenous and radial. In one embodiment, only one row in the entire grid can have its origin at any given radius. Alternatively, the grid configuration can be sector dependent i.e. the entire grid surface is composed of a number of angle sectors, for example, four sectors each of 90°, with the row configuration being essentially identical in every sector, i.e. it annularly periodically repeats. In this case, a number of rows would therefore have their origins at every selected radius, but only a single row has its origin at a given radius in every sector. The position of the origin is determined on the basis of an angle section, which is determined on the basis of specific points situated at a predetermined radius. This angle section is divided in a predefined ratio p:q, is preferably with p≠q.

As described, an inventive scattered-ray grid can be configured by determining the row arrangement such that only one row has its origin at a circle with a fixed radius. In this case, a first row that starts at the grid center is taken as a starting basis, which represents the iteration basis. Then, the first angle section, which is to be divided in the ratio p:q, is determined on the basis of this row. In this case, the two points are defined by the first row itself, the angle section is full 360° in this case. Now, this angle section is divided according to the predefined ratio for determining the position of the origin of the second row, so that the angle position of the origin of the second row is fixed at the relevant radius. Then, the position of the third row and of every further row is determined on the basis of the largest angle section, which exists between two rows that intersect the relevant circle or circle arc. The new origin is always placed in the largest angle section.

Alternatively, for a sector-by-sector row configuration, at least two rows that start in the center are used as a starting basis, by means of which rows the grid is divided into the sectors, and the origin of every further row is placed between two rows that start closer to the center, these rows defining the aforementioned points on the predetermined circle and therefore the angle section and exhibit the largest possible angular spacing of all row pairs. Therefore, the origin of a new row always lies between two rows which originate closer to the center than the origin of the new row, these two rows being the rows which are spaced furthest from one another.

Spiral-shaped density variations, even though slight may arise given the determination criterion of the angle section which is to be divided on the basis of the intervening angular space of the respective row pairs. This can be avoided in an embodiment of the invention wherein the row origins are determined starting with two rows that originate at the grid center, and the origin of the next row is placed between the row pair which has a maximum sum of the angular spacing between the rows and an additional angle value, this sum being allocated to the angle section. In this embodiment, the angle section to be divided in the ratio p:q is therefore not only determined on the basis of the actual angular spacing between the row pair, but is determined on the basis of the sum of the actual angular spacing between the row pair and an additional angle value. This additional angle value is determined by weighting, with a defined weighting factor, the respective angular spacings, on opposite sides of the adjacent row pair, between the adjacent row pair and the closest row thereto. For example, the sum of these two angular spacings (one from each side of the adjacent row pair) can be multiplied with the predefined factor, which can be <1 according to the invention, and this value can then be added with the angular spacing between the two adjacent rows. Then, the angle section, at which the largest of said sums is allocated, is divided corresponding to the predefined ratio. An even more homogenous distribution of rows results.

Apart from the scattered-ray grid itself, the invention also relates to a method for determining the position of the absorption elements of a scattered-ray grid, which are arranged in rows and which extend essentially radially relative to a center. Apart from one or more rows that start at the grid center, the origin of each row of the scattered-ray grid, or of a grid sector of the scattered-ray grid, is placed in an angle section, which is determined on the basis of two points lying on the circle or arc of circle with the origin radius $r_0+n\Delta r$ and which is divided for purposes of determining the position of the origin in a predefined ratio.

Beginning with a single row that originates in the grid center as a basis, the angle section can be determined in an iterative fashion, the angle section being 360° in this initial case and being defined as the start point as well as the end point by the first row. After this angle section has been divided, the origin of the second row is placed at the angle point deriving therefrom. For determining the origin of the third row, the row pair between which the largest angle section lies no matter how it is determined—is searched between the rows that are already present and is correspondingly divided. The iterative method is continued until a maximal radius is reached.

In an alternative embodiment of the inventive method at least two rows that both originate at the grid center are used as a starting basis. The angle space between two adjacent rows, which rows intersect the circle or arc of circle with the predetermined radius and which define the points, is determined for determining the angle section, the angle section among all row pairs being selected that exhibits the largest angular spacing. Therefore, the angle section is immediately determined from the angular spacing in this alternative. For improving the homogeneity of the row density, the angle section is selected in each iteration that has the highest sum of the angular spacing between two adjacent rows, which intersect the origin radius and which define the points, and an additional angle value. This additional angle value is obtained by weighting the respective angular spacings to the rows on opposite sides of the aforementioned adjacent rows. The predefined factor can be <1 the ratio p:q, in which the respective angle section is divided, is preferably ≠1.

Although the row configuration and the position of the rows can be iteratively determined (as described) for the entire scattered-ray grid by taking one single row that starts in the center as a basis, it has proven to be expedient to determine the position of the one row is only in one grid sector of the scattered-ray grid, which is composed of a number of grid sectors of equal size, and to "image" this row in the other grid sectors. The grid sectors are defined by means of the rows extending through the grid center.

DESCRIPTION OF THE PREFERRED EMBODIMENTS

Figure 1:
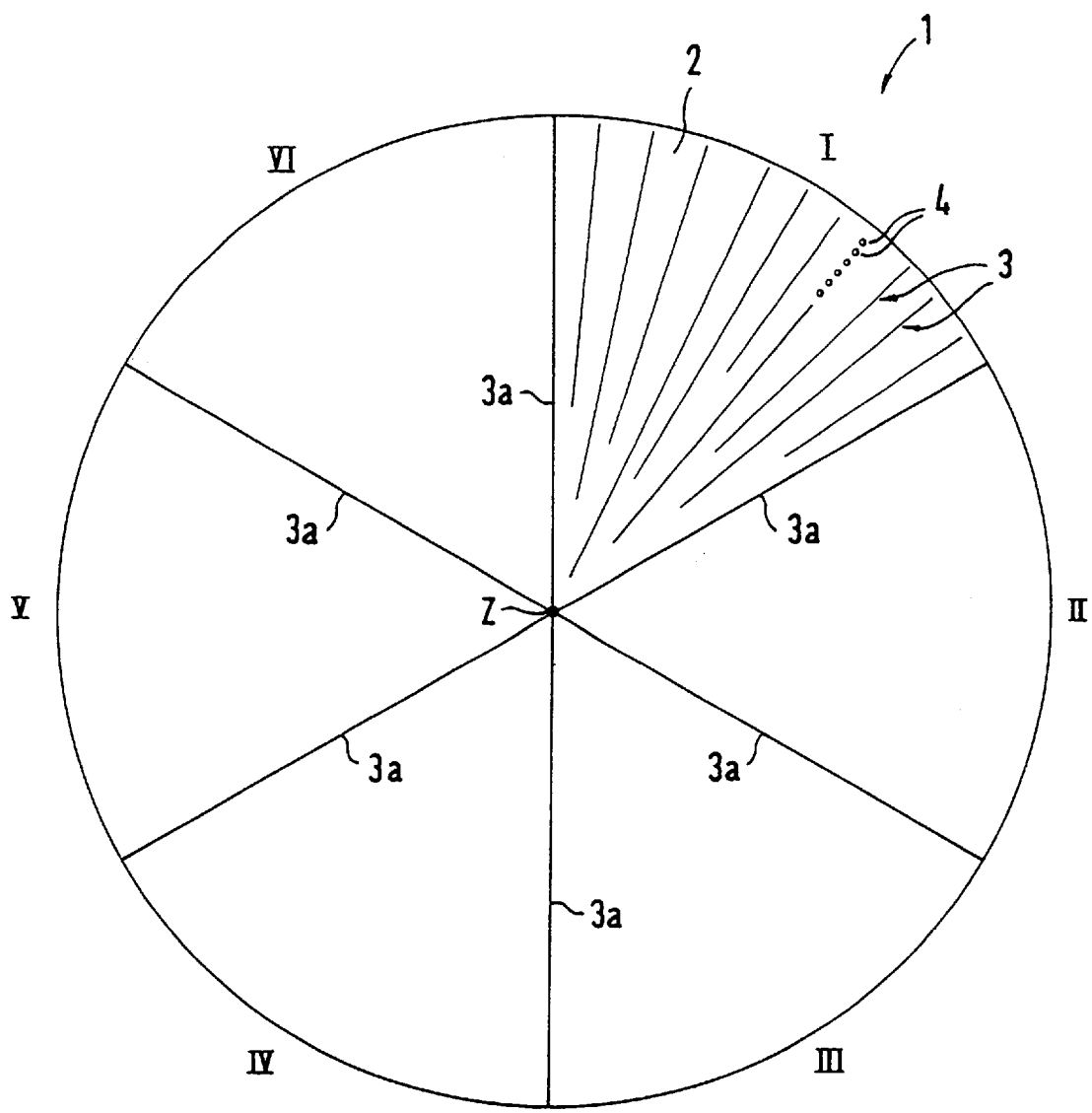
FIG. 1 shows a basic view of an inventive scattered-ray grid with a row arrangement, that is composed of a number of grid sectors that are essentially identically configured.

In the form of a basic diagram, FIG. 1 shows a plan view of an inventive scattered-ray grid 1. The grid 1 is composed of a silicon carrier 2 and of a number of rows 3 of pin-shaped absorption elements 4 made of lead, which are introduced in holes that are etched into the carrier 2. Only a few of the absorption elements 4 are specifically shown; it will be understood that each row 3 is composed of a number of such elements. The etching process ensues by means of an etching mask, which can be produced by means of a photo technique with which the configuration of the row arrangement can be fixed in a simple way. The scattered-ray grid 1 can be divided into a number of grid sectors, such as six individual grid sectors I–VI, the configuration of the rows 3 being the same in all six grid sectors. For clarity, the row arrangement is only indicated in sector I. Apart from the rows $3a$ that respectively extend through the center Z and that border the sectors, the rows 3 start at respectively different radii and are directed toward the center Z, as can be seen from FIG. 1.

Figure 2:
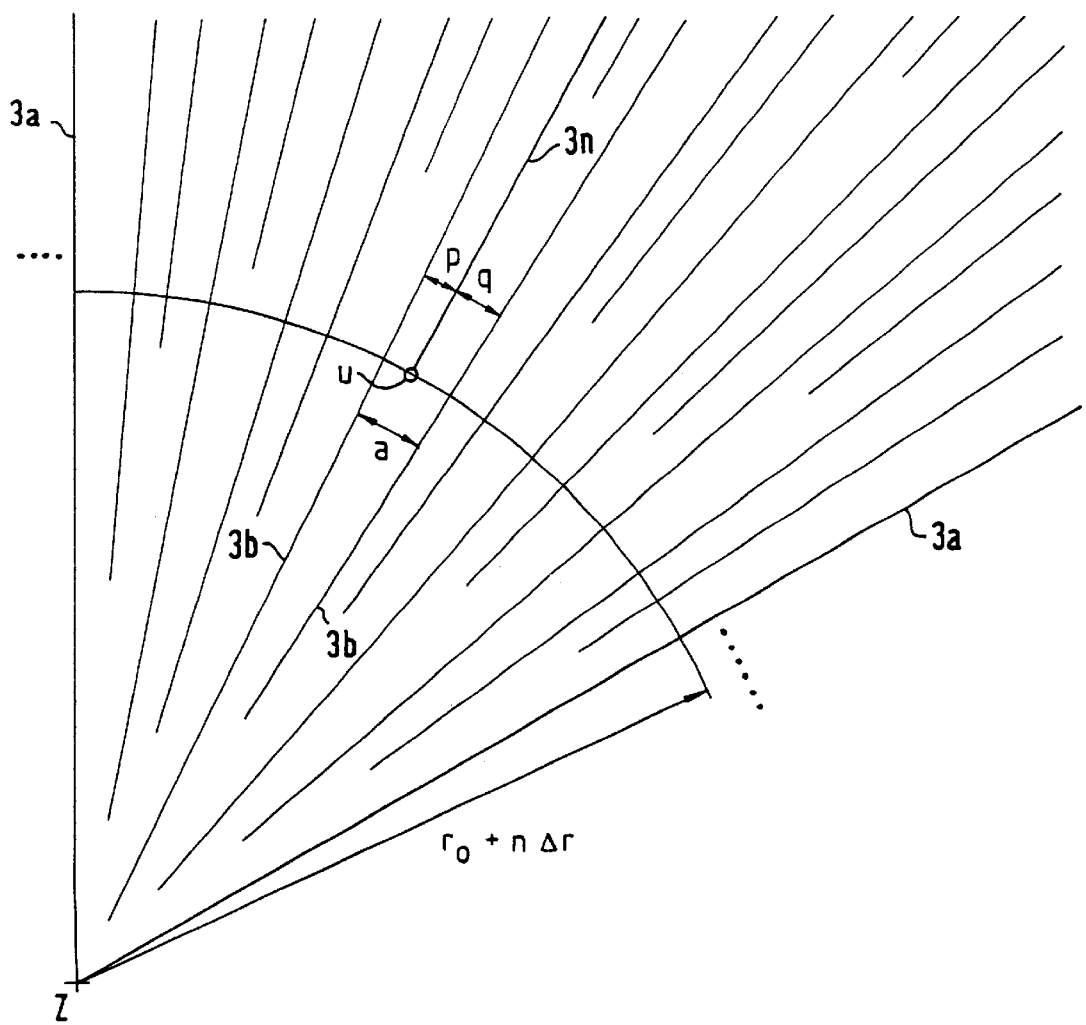
FIG. 2 is an enlarged section of the grid sector 1 of FIG. 1 for illustrating the determination of the position of a row origin according to a first embodiment of the inventive method.

FIG. 2 shows a portion of FIG. 1. The determination of the position of the origin of every row is shown in FIG. 2. Every row radially proceeds to the periphery of the carrier 2 and has its origin in the space $r_0+n\Delta r$ from the center Z. Therefore, $\Delta r$, as a radial increment, determines the density of the rows; the start radius $r_0$ optimizes the density of the rows in the center. n is an integer. A relevant space $r_0+n\Delta r$ is shown in FIG. 2 as an example. A location is now to be selected within this space, at which the origin of the (next) row $3_n$ is to be placed. The largest angular spacing between all existing adjacent rows, which intersect the circle or arc of circle with the origin radius, namely the space $r_0+n\Delta r$, is searched for this purpose. In the example, the two rows $3b$ are spaced from one another around the largest angle a. This angular spacing now determines the angle section, which is to be divided in a predefined ratio p:q, so that the exact position of the origin u of the new row $3_n$ between the two rows $3b$ results therefrom. p and q can be rational numbers or irrational numbers. The best distribution results for p≠q. In the described way, the position of each new row is determined in iterative fashion by taking the two rows $3a$ that start (originate) in the grid center as a basis.

Figure 3:
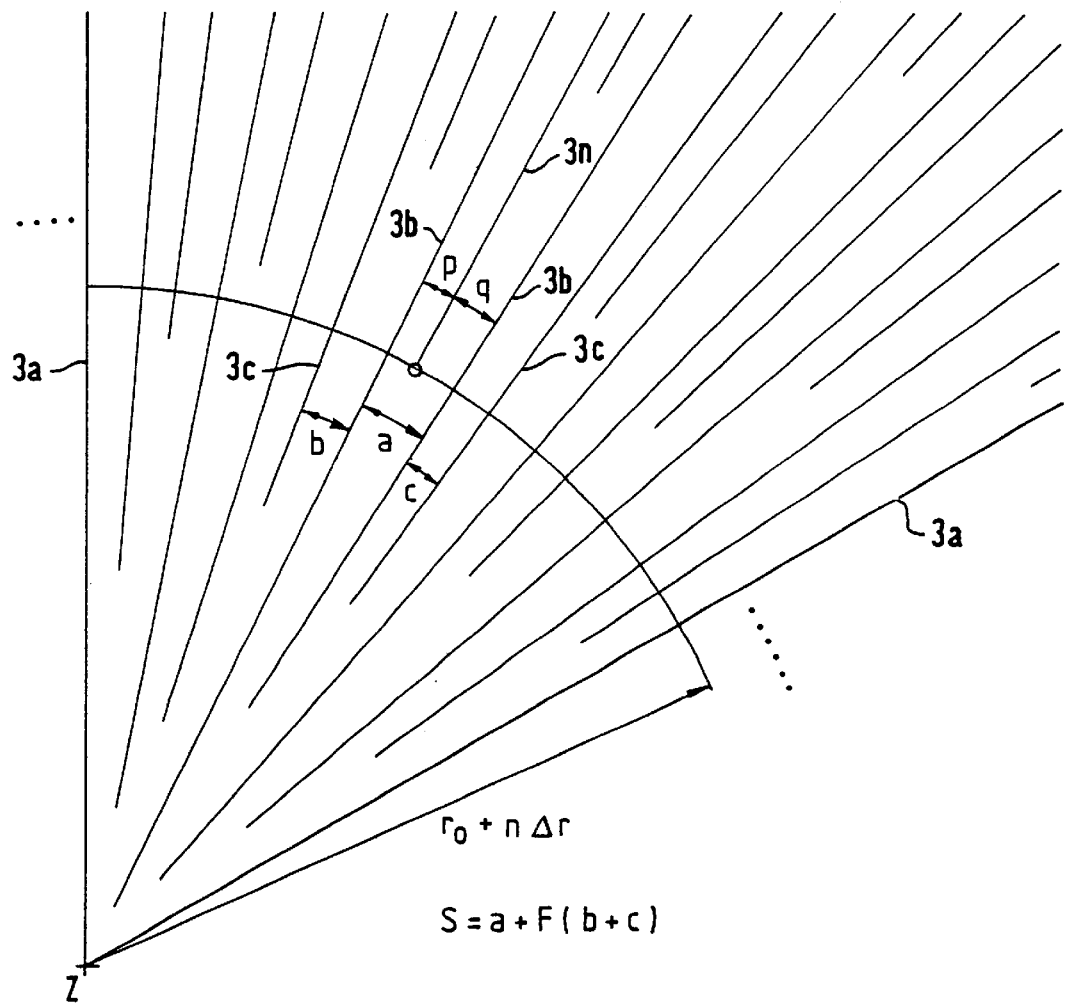
FIG. 3 is an enlarged section of the grid sector 1 of FIG. 1 for illustrating the determination of the position of a row origin according to a second embodiment of the inventive method.

The described iteration condition generates an extremely homogenous radial row pattern, but it can nevertheless exhibit spiral-shaped density variations although they are almost negligible. In order to substantially avoid such density variations, a different version of the iterative method is provided, which is explained in detail in FIG. 3. In this version, for determining the position of the new row $3n$, the angular spacing is also determined for each row pair that intersects the circle or arc of circle with the origin radius $r_0+n\Delta r$, as described with respect to FIG. 2. Subsequently, the angular spacings to the two rows respectively on opposite sides of the adjacent rows are determined. In the shown example, these are the angle spaces b and c respectively between the two pairs of rows $3b$ and $3c$. The sum S=a+F (b+c) is formed on the basis of the angle spacings a, b, c, with the sum of the two angle spacings b and c being weighted with a predefined factor F, which is <1, within the sum S. The largest sum S is now selected from the cumulative values determined for each row pair at the relevant radius, and the angle section associated with this largest sub S is divided in the given ratio p:q.

The width of a row is dependent on the diameter of the pin-shaped absorption elements 4 and is in the range of a few μm; the start radius $r_0$ is 30 μm, for example; the individual radius step or increment Δr is 100 μm, for example. In addition n is element of the natural numbers including zero. The described iterative algorithms make it possible to determine the position of the rows in a simple way, so that highly homogenous scattered-ray grids can be generated.

Although modifications and changes may be suggested by those skilled in the art, it is the intention of the inventors to embody within the patent warranted hereon all changes and modifications as reasonably and properly come within the scope of their contribution to the art.

We claim as our invention:

1. In a scattered-ray grid having a carrier on which a plurality of radiation absorption elements are disposed in a plurality of rows, said grid having a grid center and each of said rows having an origin and radiating spoke-like away from said grid center, the improvement comprising:
   at least one of said rows having an origin at said grid center; and
   the respective origins of rows, other than said at least one row originating at said grid center, being disposed at intersections of respective radial lines with at least an arc of respective circles of predetermined radii relative to said grid center, each of said radial lines dividing an angle section between two adjacent rows by a predetermined ratio.

2. The improvement of claim 1 wherein only one of said rows originates at said grid center, and all other rows in said plurality of rows have respective origins at different radii relative to said grid center.

3. The improvement of claim 1 wherein each of said radial lines divides an angle section between two adjacent rows by a predetermined ratio p:q, with p≠q.

4. In a scattered-ray grid having a carrier on which a plurality of radiation absorption elements are disposed in a plurality of rows, said grid having a grid center and each of said rows having an origin and radiating spoke-like away from said grid center, the improvement comprising:
   said grid being divided into a plurality of identical grid sectors;
   in each of said grid sectors, at least one of said rows having an origin at said grid center; and
   in each of said grid sectors, the respective origins of rows, other than said at least one row originating at said grid center, being disposed at intersections of respective radial lines with at least an arc of respective circles of predetermined radii relative to said grid center, each of said radial lines dividing an angle section between two adjacent rows by a predetermined ratio.

5. The improvement of claim 4 wherein, in each of said grid sectors, only one of said rows originates at said grid center, and all other rows in each of said sectors have respective origins at different radii relative to said grid center.

6. The improvement of claim 4 wherein each of said radial lines divides an angle section between two adjacent rows by a predetermined ratio p:q, with p≠q.

7. In a scattered-ray grid having a carrier on which a plurality of radiation absorption elements are disposed in a plurality of rows, said grid having a grid center and each of said rows having an origin and radiating spoke-like away from said grid center, a method for determining placement of the respective origins of said rows on said carrier comprising the steps of:
   originating at least one of said rows at said grid center; and
   placing the respective origins of rows, other than said at least one row originating at said grid center, at intersections of respective radial lines with at least an arc of respective circles of predetermined radii relative to said grid center, each of said radial lines dividing an angle section between two adjacent rows by a predetermined ratio.

8. A method as claimed in claim 7 comprising originating only one of said rows at said grid center, and placing the respective origins of all rows, other than said one row originating at said grid center, at different radii relative to said grid center.

9. A method as claimed in claim 8 comprising determining said different radii by starting with a predetermined origin radius and incrementing said predetermined origin radius in successive equal increments.

10. A method as claimed in claim 9 comprising:
    (a) starting with a single row originating at said grid center and dividing an angle of 360° defined by said single row originating at said grid center by a radial line at said predetermined ratio, and placing the origin of a next row at an intersection between said radial line and a circle having said predetermined origin radius;
    (b) identifying a largest angle section between said next row and said radial line and dividing said largest angle section with a new radial line at said predetermined ratio and incrementing a radius of said circle having said predetermined origin radius by said increment to obtain a new circle and placing the origin of a next row at an intersection of said new line and said new circle; and
    (c) repeating step (b) a selected number of times for successive new radial lines and with successive increments of said new circle by said equal increments.

11. A method as claimed in claim 7 comprising:
    (a) starting with a circle of a predetermined origin radius and originating two of said rows at said grid center, said two rows intersecting said circle having said predetermined origin radius respectively at two points and defining an angle section therebetween;
    (b) dividing said angle section with a line at said predetermined ratio and originating a next row at an intersection of said line and said circle having said predetermined origin radius, and thereby defining a largest remaining angle section between adjacent rows;
    (c) incrementing said circle having said predetermined origin radius by an increment to obtain a new circle and dividing said largest angle section with a new line at said predetermined ratio and originating a next row at an intersection of said new line and said new circle, and thereby defining a new largest angle section between adjacent rows; and
    (d) repeating step (c) for successive equal increments of said new circle by said increment.

12. A method as claimed in claim 11, comprising determining each new angle section by the steps of:
    identifying said new angle section as an angle section having a largest sum of said angle section plus an additional angle value, and determining said additional angle value by weighting, with a predetermined weighting factor or, angular spacings from the adjacent rows of said angle section respectively to adjacent rows on opposite sides of said angle section.

13. A method as claimed in claim 12 comprising using a value for said weighting factor which is less than 1.

14. A method as claimed in claim 7 comprising using a ratio p:q as said predetermined ratio, with p≠q.

15. In a scattered-ray grid having a carrier on which a plurality of radiation absorption elements are disposed in a plurality of rows, said grid having a grid center and each of said rows having an origin and radiating spoke-like away from said grid center, a method for determining placement of the respective origins of said rows on said carrier comprising the steps of:

dividing said grid into a plurality of identical grid sectors in each of said grid sectors, originating at least one of said rows at said grid center; and in each of said grid sectors, placing the respective origins of rows, other than said at least one row originating at said grid center, intersections of respective radial lines with at least an arc of respective circles of predetermined radii relative to said grid center, each of said lines dividing an angle section between two adjacent rows by a predetermined ratio.

16. A method as claimed in claim 15 comprising in each of said grid sectors, originating only one of said rows at said grid center, and placing the respective origins of all rows in each of said grid sectors, other than said one row originating at said grid center, at different radii relative to said grid center.

17. A method as claimed in claim 16 comprising determining said different radii by starting with a predetermined origin radius and incrementing said predetermined origin radius in successive equal increments.

18. A method as claimed in claim 17 comprising:

(a) starting with a single row originating at said grid center and dividing an angle of 360° defined by said single row originating at said grid center by a radial line at said predetermined ratio, and placing the origin of a next row at an intersection between said radial line and a circle having said predetermined origin radius;

(b) identifying a largest angle section between said next row and said radial line and dividing said largest angle section with a new radial line at said predetermined ratio and incrementing a radius of said circle having said predetermined origin radius by said increment to obtain a new circle and placing the origin of a next row at an intersection of said new line and said new circle; and (c) repeating step (b) a selected number of times for successive new radial lines and with successive increments of said new circle by said equal increments.

19. A method as claimed in claim 15 comprising:

(a) starting with a circle of a predetermined origin radius and originating two of said rows at said grid center, said two rows intersecting said circle having said predetermined origin radius respectively at two points and defining an angle section therebetween;

(b) dividing said angle section with a line at said predetermined ratio and originating a next row at an intersection of said line and said circle having said predetermined origin radius, and thereby defining a largest remaining angle section between adjacent rows;

(c) incrementing said circle having said predetermined origin radius by an increment to obtain a new circle and dividing said largest angle section with a new line at said predetermined ratio and originating a next row at an intersection of said new line and said new circle, and thereby defining a new largest angle section between adjacent rows; and (d) repeating step (c) for successive equal increments of said new circle by said increment.

20. A method as claimed in claim 19, comprising determining each new angle section by the steps of:

identifying said new angle section as an angle section having a largest sum of said angle section plus an additional angle value, and determining said additional angle value by weighting, with a predetermined weighting factor, angular spacings from the adjacent rows of said angle section respectively to adjacent rows on opposite sides of said angle section.

21. A method as claimed in claim 20 comprising using a value for said weighting factor which is less than 1.

22. A method as claimed in claim 15 comprising using a ratio p:q as said predetermined ratio, with p≠q.

* * * * *